United States Patent
Nakagomi et al.

[11] Patent Number: 6,110,724
[45] Date of Patent: Aug. 29, 2000

[54] ROTAVIRUS ANTIGEN, VACCINE AND DIAGNOSTIC AGENT FOR ROTAVIRUS INFECTIONS, AND A METHOD FOR PRODUCING THE ANTIGEN

[75] Inventors: Osamu Nakagomi; Toyoko Nakagomi, both of Akita; Shigeki Murakami; Tadashi Imagawa, both of Kagawa, all of Japan

[73] Assignee: The Research Foundation For Microbial Diseases of Osaka University, Osaka, Japan

[21] Appl. No.: 09/091,337
[22] PCT Filed: Oct. 20, 1997
[86] PCT No.: PCT/JP97/03777
  § 371 Date: Jul. 28, 1998
  § 102(e) Date: Jul. 28, 1998
[87] PCT Pub. No.: WO98/17785
  PCT Pub. Date: Apr. 30, 1998

[30] Foreign Application Priority Data

Oct. 18, 1996 [JP] Japan ................................ 8-312547

[51] Int. Cl.[7] .............................. C12N 7/00; A61K 39/15
[52] U.S. Cl. .................. 435/235.1; 435/364; 424/215.1
[58] Field of Search .................. 424/215.1; 435/235.1, 435/236, 237, 325, 363, 364

[56] References Cited

U.S. PATENT DOCUMENTS

| | | | |
|---|---|---|---|
| 4,624,850 | 11/1986 | Albert et al. | 424/215.1 |
| 5,283,172 | 2/1994 | Welter et al. | 435/5 |
| 5,474,773 | 12/1995 | Ward | 424/184.1 |
| 5,610,049 | 3/1997 | Clark | 435/235.1 |

FOREIGN PATENT DOCUMENTS

| | | | |
|---|---|---|---|
| 323708 | 7/1987 | European Pat. Off. | A61K 39/15 |

OTHER PUBLICATIONS

Nakagomi et al, Microbiol. Immunol. 34(1):77–82, 1990.
Nakagomi et al, Arch. Virol. 119:67–81, 1991.

*Primary Examiner*—Mary E. Mosher
*Attorney, Agent, or Firm*—Wenderoth Lind & Ponack L.L.P.

[57] ABSTRACT

The present invention provides a method for producing a rotavirus antigen of which the mass culture is difficult, comprising cloning a cell highly permitting the proliferation of rotavirus from a cell culture; preparing a cloned cell adapted-rotavirus strain by passaging a rotavirus in the resulting cloned cell strain and adapting the rotavirus to the cloned cell strain; culturing as a seed virus the adapted rotavirus strain or a reassortant prepared by using the adapted rotavirus strain as a parent strain; and isolating and purifying the rotavirus antigen from the culture medium of the seed virus; and additionally provides an rotavirus antigen, a vaccine against rotavirus infections, and a diagnostic agent of the diseases, as produced by using the antigen. These antigen, vaccine and diagnostic agent can make great contributions to individual fields of the fundamental research works and clinical application, relating to rotavirus infections.

2 Claims, No Drawings

ROTAVIRUS ANTIGEN, VACCINE AND DIAGNOSTIC AGENT FOR ROTAVIRUS INFECTIONS, AND A METHOD FOR PRODUCING THE ANTIGEN

BACKGROUND OF THE INVENTION

1. Field of the Invention

The present invention relates to rotavirus antigens of which the mass production via cell culture are difficult, a vaccine against rotavirus infections and a diagnostic agent of the diseases and methods for producing the same. More specifically, the present invention relates to a vaccine and a diagnostic agent useful for the prophylaxis and diagnosis of rotavirus infections, and rotavirus antigens as the effective ingredient thereof. The present invention makes contributions to the prophylaxis and diagnosis of rotavirus infections in humans, in particular.

2. Description of the Related Art

Rotavirus is a pathogenic microorganism causing diarrhea in humans, monkeys, dogs, cats, horses, cows, pigs, sheep, rabbits, rats, chickens, turkeys and the like, and is widely distributed all around the world. Rotavirus infections in humans in particular have been drawing attention, as vomiting and diarrhea in babies, winter-term diarrhea in babies, diarrhea with white feces, kid pseudo-cholera and the like. The prophylaxis and diagnosis thereof have been expected strongly at a worldwide scale.

What will be described below has been known concerning rotavirus.

Morphology and Genome Structure

According to the 6-th report by the International Committee of Taxonomy of Viruses, the virus belongs to the family Reoviridae, and is in an exact icosahedron of a diameter of about 70 nm, comprising a double capsid structure of inner and outer capsids (three layers in total, including the intermediate layer) with no envelop, and has a core of a diameter of about 50 nm at the center of the inner capsid. Inside the core is present a genome, comprising a linear double-stranded RNA with 11 segments, and the sizes of these genome segments are within a range of 0.6 to 3.3 kbp ("Virus Taxonomy: Sixth Report of the International Committee of Taxonomy of Viruses", Archives of Virology, Supplement 10, pp.219–222, 1995).

Genotype and Serotype

From the standpoint of developing a vaccine and a diagnostic agent therefor, attention has been focused particularly on the fourth genome segment and the ninth genome segment (corresponding to the seventh or eighth genome segment in some strain), among the 11 genome segments described above. Rotavirus strains isolated worldwide have been classified into six groups (serogroups) from A to F and each group is divided into various serotypes; for convenience, additionally, rotavirus strains are broadly grouped depending on the genotypes. These isolated strains have a variety of both antigenicities and genotypes ("Fields Virology", 3rd ed., vol.12, pp.1625–1629, edited by B. N. Fields et al., Lippincott-Raven Publishers, 1996, USA). The following description is about what is described immediately above.

The fourth genome segment encodes the structure protein VP4 exposed in a spike form on the surface of the virus particle, and it is reported or assumed that VP4 may functionally be involved in blood cell agglutinins, neutralizing antigens, the infectivity promoted by protease, pathogenicity, membrane fusion, adsorption to cells, and so on. Based on the amino acid sequence of the VP4 and the homology with the RNA or cDNA of the gene, rotavirus stains are currently classified into 20 genotypes (referred to as "P genotype" hereinbelow); and based on the neutralizing test, rotavirus strains are also classified into 10 or 14 serotypes (referred to as "Serotype P" hereinbelow).

The ninth genome segment (seventh or eighth genome segment in some strain) encodes the outer capsid VP7 of the virus particle, and it is reported or assumed that the VP7 may possibly function to retain the epitope of neutralizing antigen and two hydrophobic regions. Based on the neutralizing test of the VP7, rotavirus strains are classified into 14 serotypes (referred to as "serotype G" hereinbelow).

Classification of Rotavirus Strains

Among a great number of various isolated strains reported previously ("Fields Virology", 3rd ed., vol.2, p.1627), a typical human rotavirus strain of the group A and the following strains isolated and reported by the present inventors, namely AU-1 (Journal of Clinical Microbiology, 25, 1159–1164, 1987), AU32 (Microbiologyand Immunology, 34, 77–82, 1990) and AU64 (Archives of Virology, 19, 67–81, 1991), are broadly classified as follows in Table 1.

TABLE 1

| Name of strain | Serotypes G and P [genotype] |
|---|---|
| Wa | G1P1A [8] |
| DS-1 | G2P1B [4] |
| P | G3P1A [8] |
| AU-1 | G3P3 [9] |
| Hochi | G4P1A [8] |
| ST3 | G4P2A [6] |
| AU32 | G9P1A [8] |
| AU64 | G1P1B [4] |

Detection Frequency of Serotype

According to about 20 research reports worldwide about the detection frequency of the serotype G of rotavirus, type G1 is main, occupying about 60 to 85% in Japan, European countries, Australia and Central Africa and the like, while the remaining part is primarily occupied by types G2 and G3. In India, Thailand, Bangladesh, Mexico and the like, alternatively, G1, G2 G3 and G4 are detected in a sporadic fashion, and the ratio of them in total ranges at about 20 to 80%, and the sporadic occurrence of other types except these types is also observed prominently.

Virus Culture

Because rotavirus isolated from monkeys and cattle is generally grown in a culture cell in a relatively ready manner, the culturing or passages thereof is not essentially hard. However, so-called abortive infection occurs during the passage of human rotavirus in cell culture, characteristically involving the generation of a virus antigen impossible of serial passages for obtaining the infectious virus particle, and therefore, the virus passage is very hard. Hence, a procedure has been designed, comprising preparing a reassortant between a human rotavirus with a low growth potency and a monkey- or cow-derived rotavirus with a high growth potency, to improve the growth potency of human rotavirus, or comprising inoculating a human rotavirus preliminarily treated with trypsin into a monkey-derived cell strain M104 (ECACC No. 85102918) and AGMK (African Green Monkey Kidney) cells, and thereafter injecting the rotavirus to the roller tube culture using a maintenance medium supplemented and mixed with trypsin. Currently, almost all human rotaviruses of the group A can directly be cultured or isolated in laboratories. However, even through the above roller tube culture, a virus antigen at an amount required for the production of vaccine or diagnostic agent cannot be recovered. Still currently, the culturing or passaging of rotaviruses except the viruses of the group A is at a very difficult stage.

Host of Virus Culture

For the culturing of permissive cells permitting the proliferation of rotavirus, the following individual cell strains have been known, other than the MA104 and GMK cells; individual cells of FBK (fetal bovine kidney), CMK (cercopithecus monkey kidney), MK (crab-eating macaque kidney), etc.; individual cell strains of monkey-derived CV-1, FRh L2, BSC-1, and Vero cell and dog-derived MDCK, human intestinal epidermis-derived CaCO-2, etc. (WO 92/01784, Japanese Patent Laid-open No. 06-328107, the "Fields Virology", 3rd ed., vol.2, pp.1647–1648, pp. 1661–1162). For the mass production of rotavirus antigen for the purpose of producing a vaccine, furthermore, cell strains for use in producing other virus vaccines, such as Vero, DBS-FLC-1, DBS-FLC-2, DBS-FRh L2, ESK-4, HEL, IMR-90, MRC-5, MRC-9, WI-38, and WRL68, can be utilized ("ATCC Microbes & Cells at Work", 2nd ed., p.144, American Type Culture Collection 1991, USA).

Vaccine

Various vaccines against human rotavirus infections have been attempted and developed since around 1985. The main stream lies in the development of a live vaccine by so-called Jennerian approach, wherein a non-human-derived attenuated vaccine with a similar antigenicity is used as vaccine in place, like small pox vaccine; for example, it has been known clinical trials of live vaccines by using a cow- or monkey-derived attenuated vaccine or an attenuated reassortant between two virus strains each derived from both humans and cow or from both humans and monkeys (WO 92/01784; EPO 130906; Japanese Patent Laid-open No. 06-328107; "Modern Vaccinology", pp. 213–229, edited by E. Kurstak, Plenum Medical Book Company 1994, USA; "Vaccines", 2nd ed., pp. 809–822, edited by S. A. Plotolokin and E. A. Mortimer, W. B. Saundors Company 1994, USA; "The Jordan Report—Accelerated Development of Vaccines 1996", p. 46 and p.68, National Institute of Health issued, USA). As the data of the clinical trials of these live vaccines or the oral dosing thereof has been accumulated, however, it has been remarked increasingly that the prophylactic effect is not sufficient. Currently, therefore, an attempt has been made for the production of a vaccine based on a different idea from the idea of the Jennerian approach.

Diagnostic Agent

Antigens are mainly detected with polyclonal or monoclonal antibodies, and kits for EIA (enzyme immunoassay), ELISA (enzyme-linked immunosorbent assay), latex agglutination and passive hemagglutination, for example, are now commercially available. Diagnostic methods at gene levels by means of PAGE-SS (polyacrylamide gel electrophoresis with silver stain), PCR (polymerase chain reaction) and the like are now developed ("Principles and Practice of Infectious Diseases", 4th ed., vol.2, pp. 1450–1451, edited by G. L. Mandell et al., Churchill Livingstone 1995, USA). Because no diagnostic agent by means of virus antigens for antibody detection has been distributed yet, data relating to the temporal variation of various antibodies against rotavirus antigens in patients is still likely to be insufficient, although such data is extremely useful for the elucidation of rotavirus infections and the countermeasure thereof including prophylaxis and therapeutic treatment.

In such circumstance concerning human rotavirus as has been described above, the present invention has been attained. It is an object of the present invention to overcome the current stage such that the mass production of rotavirus antigen via cell culture is very difficult, and provide a method for producing a rotavirus antigen at a large scale, the antigen being required for producing a vaccine against rotavirus infections, and a diagnostic agent of the diseases.

It is the other object of the present invention to provide the antigen recovered by the method described above, a vaccine against rotavirus infections and a diagnostic agent of the diseases, which are to be produced by using the antigen.

SUMMARY OF THE INVENTION

So as to overcome the problems, the present application provides the following inventions.

More specifically, a first aspect of the present invention is a method for producing a rotavirus antigen, comprising cloning a cell highly permitting the proliferation of rotavirus from a cell culture; preparing a cloned cell adapted-rotavirus strain by passaging a rotavirus in the resulting cloned cell strain and adapting the rotavirus to the cloned cell strain; culturing as a seed virus the adapted rotavirus strain or a reassortant prepared by using the adapted rotavirus strain as a parent strain; and isolating and purifying the rotavirus antigen from the culture medium of the seed virus.

In a preferable embodiment of the first aspect of the present invention, the culture cell is Vero cell (ATCC CCL 81).

In another preferable embodiment of the first aspect of the present invention, the cloned cell strain is Vero CL-9 (FERM BP-6028).

As a still other preferable embodiment of the first aspect of the present invention, the rotavirus is human rotavirus strain AU32n and/or AU64n.

A second aspect of the present invention is the rotavirus antigen recovered by the aforementioned method.

A third aspect of the present invention is an inactivated antigen prepared by further inactivating the rotavirus antigen of the second aspect of the present invention with an inactivator.

A fourth aspect of the present invention is a vaccine against rotavirus infections, the vaccine containing the rotavirus antigen of the second aspect of the present invention or the inactivated antigen of the third aspect of the present invention at an amount for causing an immune response.

A fifth aspect of the present invention is a combined multivalent vaccine for rotavirus infections, containing two or more antigens at an amount required for an immune response, wherein the antigens are the rotavirus antigen of the second aspect or the inactivated antigen of the third aspect and the serotypes or genotypes thereof are different from each other.

A sixth aspect of the present invention is a diagnostic agent, containing the rotavirus antigen of the second aspect or the inactivated antigen of the third aspect at an amount required for an antigen-antibody response.

A seventh aspect of the present invention is a cloned cell strain Vero Cl-9 (FERM BP-6028).

An eighth aspect of the present invention is a cloned cell adapted-human rotavirus strain AU32n.

A ninth aspect of the present invention is a cloned cell adapted-human rotavirus strain AU64n.

In this application, the term "cloned cell strain" means a culture cell of a clone singly composed of the progeny of a single cell (species).

The term "adaptation" means the promotion of the mutation or selection of virus proliferation potency to fit the proliferation potency to the purpose, so that a virus mass production might be possible under constant conditions of the cell type and temperature for virus culture. For example, a virus adapted to a certain cell can proliferate well in the cell and a virus adapted to low temperature can proliferate well at the low temperature.

The term "permissive" means the "permissive" property of a cell to permits virus proliferation. For example, the term "rotavirus permissive cell" means that rotavirus can proliferate or can be cultured in the cell.

The term "cloned cell-adapted virus strain" means a virus which is adapted to a cloned cell strain, by serial passages of the virus in the said cloned cell strain.

Other terms are apparently shown in the following Description of the Preferred Embodiments.

DESCRIPTION OF THE PREFERRED EMBODIMENTS

Each invention in this application can be practiced, by carrying out the following first to fourth processes.

First process: cloning a cell highly permitting the proliferation of rotavirus, namely highly permissive cell, from a cell culture.

Second process: preparing a cloned cell adapted-rotavirus strain which is adapted to the cloned cell strain recovered at the preceding process, under serial passages of the virus in the cloned cell strain, namely an adapted rotavirus strain capable of extremely actively or highly proliferating in the cloned cell strain. If needed, a reassortant is prepared by using the adapted rotavirus strain as a parent strain. The rotavirus to be used at the first process is not necessarily the same as the rotavirus cultured at the second process.

Third process: mass producing rotavirus antigens, namely complete rotavirus particle, incomplete rotavirus particle, antigenic protein, genome, gene and the like, by culturing as a seed virus the adapted strain or the reassortant recovered at the preceding process.

Fourth process: preparing and producing vaccines, diagnostic agents, and reagents and the like, by purifying, processing or modifying the complete rotavirus particle, incomplete rotavirus particle, antigenic protein, genome, gene and the like, as recovered at the preceding process.

The processes are now described below sequentially in order.

Culture Cell to be Used at the First Process

As the subjective culture cell for cloning a cell highly permitting the proliferation of rotavirus, use is made of various cells or cell strains as previously described in the section of the "Host for virus culture" in the Description of the Related Art. For use, then, a culture cell in which the absence of adversely affecting contaminated factors or cancer genes is concluded, for example Vero cell (ATCC CCL 81), is preferably used.

Rotavirus for use at Second Process As the rotavirus to be passaged in and adapted to the cloned cell strain recovered at the aforementioned process, use is made of isolated strains described in the reference ("Fields Virology", 3rd ed., vol.2, p.1627, Archives of Virology, 19, 67–81, 1991, etc.) or appropriate rotavirus strains. Particularly, a strain to be passaged during cell culture with much difficulty or a virus strain promising for the increase of the production of antigens is preferable. For example, known strains of AU-1, AU32 and AU64, and novel human rotavirus strains with an appropriate passage history as a virus strain for vaccine production, such as AU32n and AU64n, which are to be provided in accordance with the present invention, are preferable.

Cell Culture Medium, and Medium for Virus Growth

Known and commercially available media, for example 199 medium, MEM (Eagle's Minimum Essential Medium), BME (Eagle's Basal Medium), Hanks solution, and Dulbecco's phosphate buffered saline (PBS), may be used. The compositions and preparative methods thereof are described in detail in general texts relating to virus experiments, cell culture and tissue culture (for example, "Cells & Tissue Culture; Laboratory Procedures", 2 volumes in total, edited by A. Doyle etal., John Wiley & Sons 1993, USA) and catalogs of commercially available products. Such media and salt solutions may be supplemented and modified with auxiliary agents or additives. As the additives, use may be made of routine substances; it is selected from for example commercially available human serum, fetal calf serum, antibiotics, sodium hydrogen carbonate, sodium chloride, non-essential amino acids and the like, for use at an appropriate amount. For example, the final concentrations of the additives to be added and mixed with one liter of a culture medium are as follows; sera at about 3 to 25% (V/V); sodium hydrogen carbonate at about 1 to 6 g; sodium chloride at about 0.1 to 0.25 mole; and non-essential amino acids at standard amounts as described in the product catalogs. It has been known that protease or trypsin in particular is preferably added and mixed into rotavirus proliferation media. Herein, the final trypsin concentration in the media for rotavirus growth is about 0.1 to 10 $\mu$g/ml.

Cell Culture and Cell Cloning

The passage of a cell strain generally comprises preparing a cell suspension at about $1\times10^5$–$4\times10^5$ cells/ml in a cell culture medium, and passaging the suspension of a volume about 1/10 to 1/5-fold the volume of a culture container, for example about 10–20 ml in a 100-ml container and culturing then the cell at about 37° C. So as to peel off cells having formed a monosheet on the bottom of the container from the area of the culture container and then disperse the cells, generally, use is made of a trypsin solution of about 0.25% (W/V) as the final concentration, which is preliminarily prepared in PBS from which both Ca and Mg ions are eliminated.

According to the routine method ("Cells & Tissue Culture; Laboratory Procedures", vol.1, pp. 4B:3, supra.), cells are cloned. Cell cloning may satisfactorily be effected, for example, by a method (colony forming method) for preparing a clone singly composed of the progeny of a single cell, comprising peeling off a monosheet of cultured cells in the trypsin solution and dispersing the sheet in the cell culture medium to prepare a suspension of a free cell (about 1 to 5 cells/ml), then inoculating the suspension into culture containers, for example petri dish or microtest plate, for culturing. Recovered colonies are independently cultured to increase the cell number, whereby a cloned cell or a cloned cell strain can be recovered.

Virus Culturing and Passage and Adaptation

The temperature for virus culture in a host of cell culture is generally about 20 to 37° C., and the culture duration is about 2 to 16 days. Stationary culture or roller tube culture may satisfactorily be used. The supernatant of the culture fluid after culturing is subjected to virus passage as a virus suspension. Virus passaging is effected by sequentially inoculating virus suspensions in fresh culture cells to proliferate the virus. By repeating the virus passaging in a specific cell about 2 to 50 times, preferably about 3 to 20 times, a specific cell-adapted virus strain very highly proliferating in the cell can be recovered. By preparing a reassortant between the adapted virus strain as the parent strain and another virus strain, the high proliferation potency of the adapted virus can be transferred into a different virus strain. By mixing together a rotavirus strain inactivated with the irradiation of ultraviolet ray (UV) and the adapted virus strain (parent strain) and culturing the mixture, thereby inducing the reassortment of the genome segments of the viruses of both the strains, and eliminating the parent strain virus with an anti-parent strain neutralizing antibody, a remaining infectious virus can be recovered as a reassortant.

Selection of Highly Permissive Cloned Cell Strain for Rotavirus

By inoculating and culturing rotavirus in each cloned cell, the numbers of infectious viruses and virus particles or the level of virus antigen, which are generated through the virus proliferation, is determined. In this case, it is important to determine the extent of the proliferation due to the difference in MOI (multiplicity of infection), namely so-called virus production level, high or low, depending on the difference in virus inoculation level, by a method described below. By screening a cloned cell in which the virus can highly proliferate by using such measured values as markers, a highly permissive cloned cell strain can be yielded. The measurement is done by plaque forming method (counting PFU (plaque forming unit)), focus forming method (counting FFU (focus forming unit)), ELISA, IME (immune electron microscopy) and the like. Herein, FFU is counted by fluorescent antibody technique comprising staining an infectious cell region formed due to the infection and proliferation of the virus with a fluorescent dye FITC (fluorescein isothiocyanate)-labeled antibody, by EIA (enzyme immunoassay) and the like.

Mass Production and Preparation of Virus and Antigen

By using a cell culture of a highly permissive cloned cell strain as a host and culturing a virus strain adapted to the cell strain, the virus and an antigen are produced at a large scale. More specifically, after the termination of culturing, a supernatant of a virus culture fluid after centrifugation at a low speed (for example, a supernatant of a suspension of a virus infected cell after freezing and thawing in dry ice and an organic solvent) is collected, to prepare a complete virus particle and the antigen. Such preparation may be used as the virus suspension as it is. The suspension is possibly disinfected by membrane filtration, or antibiotics may satisfactorily be added to the suspension. The virus antigen in the suspension and the like may be concentrated and purified by membrane concentration, density gradient ultra-centrifugation, ultra-centrifugation on a sucrose cushion. The virus suspension is overlaid on a sucrose solution as a cushion, for example, for subsequent ultra-centrifugation, to precipitate the virus antigen on the bottom of a centrifuge tube, and the precipitate is again suspended to prepare a purified virus antigen.

Preparation of Vaccine Bulk Solution

A vaccine bulk solution can be prepared by using the virus suspension or purified virus antigen. As the antigen for vaccine, furthermore, use may be made of complete virus particles, incomplete virus particles, protein of the virion structure for example VP4 and VP7, neutralizing reaction epitope region, and modified structural protein after translation and the like in the virus suspension, and protein of non-virion structure and modified protein after translation, and protective antigens against infection and the like. Such antigens for vaccine can be immobilized with inactivating agents, so that the steric structure can be stabilized. As the inactivating agent, for example, use may be made of formalin, phenol, glutaraldehyde, β-propriolactone and the like, which are added into a vaccine bulk solution prior to or after the preparation of the solution. If used, formalin is added at an amount of about 0.005 to 0.5% (V/V), and the inactivation temperature is about 2 to 38° C. and the inactivation time is about 5 to 180 days. When the antigenicity is deteriorated through such inactivation, however, an instrumental measure is required for modifying the inactivation conditions, including for example the reduction of the amount of the inactivator, the addition of neutral amino acid or basic amino acid, and the lowering of the inactivation temperature. The free formaldehyde remaining at the inactivation process can be neutralized by adding an equal amount of sodium hydrogen sulfite or can be eliminated during dialysis. The preparation thus produced is subjected to the following process as a vaccine bulk solution.

Preparation of Vaccine

The vaccine bulk solution is diluted for example in a culture medium BME, to adjust the antigen level in the vaccine to the level required for antibody generation.

Then, a stabilizer for enhancing the heat resistance of the vaccine or an adjuvant as an auxiliary agent for enhancing the immunogenicity, may be added and mixed into the bulk solution. For example, use may be made of sugars and amino acids as stabilizers; and mineral oil, vegetable oil, alum, aluminum phosphate, bentonite, silica, muramyl dipeptide derivatives, thymosin, interleukin and the like as auxiliary agents.

For the purpose of the induction of mucosal immunity or local immunity, the virus antigen in the vaccine bulk solution may be treated or modified. For the induction, a technique relating to DDS (drug delivery system) using for example liposome, emulsion, microcapsule, microsphere, polylactic acid, and polyglycolic acid is applicable.

Then, the vaccine solution is divided into a vial of an appropriate volume, for example about 1–20 ml, followed by stopping and sealing, and the resulting vaccine solution is subjected to use. The vaccine is not only at a liquid state but is also subjected to use as a dry formulation by freeze-drying the solution after division. For the purpose of oral administration, the vaccine solution is possibly processed into for example syrups or candies.

So as to guarantee the quality prior to use, namely during the production processes thereof and at the division stage of the solution in small portions, the prepared vaccine formulation is tested as to the safety and efficacy, to verify the appropriateness of the solution as vaccine. Such testing can be practiced following the standard for a formulation similar to the rotavirus vaccine of the present invention, for example, the Regulation "Inactivated Acute Polymyelitis Vaccine Standard" defined in "Biological Formulation Standard" according to the Pharmaceutical Law (Law No.145, 1960) and Notification No.315, 1960 of the Ministry of Health and Welfare and Notification No.337, Revision, 1961 of the Ministry of Health and Welfare; both the Regulations "Japanese B Encephalitis Vaccine" and "Dry Japanese B Encephalitis Vaccine" as defined in the "Biological Formulation Standard" according to the aforementioned Pharmaceutical Law and Notification No.217, 1993 of the Ministry of Health and Welfare; or the Regulation "Dry Tissue Culture Inactivated Type A Hepatitis Vaccine" defined in the "Biological Formulation Standard" according to the aforementioned Pharmaceutical Law and Notification No.332, 1994 of the Ministry of Health and Welfare; and the like.

Dosage of Vaccine

Vaccine inoculation is practiced, by inoculating the vaccine subcutaneously for example at a dose of about 0.25 to 0.5 ml; by orally administering one dose of about 1.0 ml; or by injecting about 0.05 ml of the vaccine into oral cavity. Furthermore, such inoculation is preferably practiced one to three times at an interval of about 2 to 4 weeks. However, the vaccine dosage is not limited to the examples described above.

Preparation of Diagnostic Agent

In the same fashion as described above, a virus suspension or a purified antigen or the like is prepared, which is then provided as a diagnostic antigen (for example, antigens for precipitation reaction, agglutination reaction, neutralizing reaction, fluorescent antibody technique, enzyme immunoassay, radioimmunoassay, etc.). By inoculating the diagnostic antigen or the vaccine bulk solution peritoneally, subcutaneously, intra-muscularly in animals (for example, rabbit, guinea pig, mouse, etc.), antibodies may be prepared from the sera of the animals. The antibodies are provided for antigen assay by the various diagnostic methods described above. The diagnostic antigens and antibodies in accordance with the present invention are diluted and adjusted to an amount required for inducing antigen-antibody reaction, prior to use. Furthermore, the genome and its CDNA fragment of rotavirus in accordance with the present invention may be provided for example as probe reagents and identification reagents for gene diagnosis.

The present invention will now more specifically be described in further detail in the following examples, but the invention is not limited to the examples.

EXAMPLE 1

(1) Cell Cloning

Vero cell (ATCC CCL 81) was cultured in a cell culture medium MEM supplemented with FCS (manufactured by Gibco, Co., USA) at a final concentration of 9% (V/V) in a container with a culture area of 25 $cm^2$ at 37° C., to form a monosheet. The monosheet was peeled off in 0.25% (W/V) trypsin (trypsin 1: 250; manufactured by Difco, Co., USA) solution from the area of the culture container, to disperse the cells to prepare the cells into a free single cell, and thereafter, the cells were collected with centrifugation at a low speed (1500 rpm, 5 minutes), to prepare a suspension of a free single cell at 2 cells in cell number/ml in the culture medium. The suspension was inoculated in 0.2 ml portions into each well of a 96-well microtest plate (Falcon Microtest III Plate; manufactured by Becton Dickinson, Co., USA) and was then cultured in a $CO_2$ incubator at 37° C. for 14 days, to form a colony singly composed of the progeny of the single cell on the surface of each well. The cells in each of the individual colonies were sequentially passaged three times into a larger container, thereby increasing the number of the cells, whereby 40 in total of cell suspensions of individual Vero cell colonies were recovered.

(2) Screening of Rotavirus Permissive Cloned Cell Strain

Rotavirus in each of the cloned cells in total of 40 as recovered above in (1) was cultured and proliferated, to assay the rotavirus antigen in the culture supernatant by ELISA, and then, a cloned cell strain with a far higher antigen titer than the titer of the Vero cell prior to cloning was screened as described below in a) to c).

a) Culturing of Virus in Each Cloned Cell

Each cloned cell was assigned to eight wells in one cross row of the microtest plate (96 wells; 8 wells in cross direction ×12 wells in lengthwise direction), and then, 40 in total of the cell suspensions of individual clones were independently inoculated at 0.2 ml/well, for incubation at 37° C., to form a monosheet of each clone. Subsequently, the culture fluid in each well was exchanged to a fresh MEM with no addition of serum for further culturing overnight. Into the cells in each well was added 0.05 ml/well of rotavirus AU64 strain fluid activated with trypsin treatment in a medium for virus growth described below (provided that the final trypsin concentration was 20 μg/ml) at 37° C. for 20 minutes, and then, the cells were left to stand at 37° C. for 30 minutes, so that the cells could adsorb the virus. Thereafter, an MEM with addition of trypsin to a final concentration of 0.5 μg/ml as a medium for virus growth was added at 0.2 ml/well, for culturing and proliferating the virus at 37° C. for 7 days. After the termination of the culture, the culture fluid in each well was subjected as a virus suspension (sample) to the assaying of virus antigen described below. As a comparative control, herein, the Vero cell prior to cloning was used.

b) Assay of Virus Antigen (primary screening)

The antibody against rotavirus of group A (IgG purified from per-immunized serum in guinea pigs) was diluted in 50 mM carbonate buffer, pH 9.6, to prepare an antibody solution at a concentration of 1.0 μg/ml. The antibody solution was added at 0.1 ml/well into a 96-well test plate for ELISA (ELISA-PLATE; manufactured by Greiner, Co., Germany), which was then left to stand at 4° C. overnight, to adsorb the antibody on the well surface. After adsorption, each well was rinsed in a rinse solution [PBS containing Tween 20 at a final concentration of 0.05% (W/V)]. Meanwhile, each virus suspension described above was diluted 5-fold in an antigen dilution solution [Block Ace (manufactured by Snow Brand Milk Industry, Co. Ltd.) was diluted by 10-fold in deionized water], and the resulting prepared samples each were added in 0.1-ml portions into each well, for primary reaction at 25° C. for 90 minutes. After rinsing the wells with the aforementioned rinse solution, then, peroxidase-labeled anti-rotavirus goat antibody (manufactured by Viro Stat Co., USA) was diluted 2,000-fold in the antigen dilution solution, and the resulting antibody solution was added at 0.1 ml/well, for secondary reaction, againat 25° C., for 90minutes. Subsequently, each well was rinsed in the rinse solution, followed by addition of a substrate solution [0.5M citrate—phosphate buffer, pH 5.0, containing o-phenylenediamine (manufactured by Wako Pure Chemical Industries, Co.) at a final concentration of 0.4 mg/ml and an aqueous 35% (V/V) hydrogen peroxide solution (Wako Pure Chemical Industries, Co.) at 0.1 ml/well, for chromogenic reaction at ambient temperature for 10 minutes, followed by further 0.05 ml/well addition of 4N sulfuric acid to terminate the reaction. After the termination of the reaction, the absorbance (OD) of each well was counted at a monochromatic ray at a wave length of 490 nm. As the results of the aforementioned primary screening, six samples with OD of 5-fold or more the OD of the comparative control, were selected, and the corresponding cloned cell strains were then subjected to the following secondary screening.

c) Assay of Virus Antigen (secondary screening)

In the same manner as described above in (1), cells of the six cloned strains were cultured in a microtest plate, and simultaneously, the AU64 strain was cultured and proliferated in the cells in each well. So as to observe the extent of growth, depending on the difference in MOI, additionally, the virus suspension was serially diluted 4-fold, and each dilution series was assigned to one row in the lengthwise direction and two wells in the cross row. Additionally, the virus antigen was assayed by ELISA, in the same manner as for the primary screening. Consequently, three highly permissive cloned cell strains highly permitting the proliferation of rotavirus could be recovered, and these strains were individually designated as Vero CL-9 (FERM BP-6028), Vero CL-16 and Vero CI-81-7.

EXAMPLE 2

Adaptation of Rotavirus:

Individual cloned cell strains recovered in Example 1, namely Vero CL-9, Vero CL-16 and Vero CI-81-7, were cultured at 37° C. in a cell culture medium MEM [supplemented with FCS (manufactured by Gibco, Co.; USA) at a final concentration of 9% (V/V)], along with the comparative control Vero cell prior to cloning, to form monosheets of the individual cells. As culture containers, two tissue culture test tubes were used per each cell strain. After the formation of the monolayer, the media in the individual containers were exchanged to a fresh MEM with no addition of serum, for additional culturing overnight. Then, the virus suspension (0.2 ml) of AU64 strain was inoculated into the cells in the individual containers and was then left to stand at 37° C. for 60 minutes, to adsorb the virus onto the cells, followed by discarding the inoculation solution. Subsequently, an MEM [supplemented with trypsin type IX (manufactured by Sigma, Co., USA) at a final concentration of 0.5 µg/ml] as a virus proliferation medium was added at 1 ml/container, for roller tube culture of the virus at 37° C. for 7 days. After the termination of culturing, the culture fluid was collected and stored as a virus suspension at −80° C. By repeating the same virus culturing by using each of these virus suspensions, the virus was passaged over 7 generations. By the following fluorescent antibody technique (FA) and enzyme antibody technique (EIA), the infectious titer (FFU) of the virus suspension of each generation was assayed.

Into each cloned cell strain and the comparative control cell after culturing in a chamber slide (manufactured by Nunc, Co., USA) in the same manner as described above, were added the virus suspensions serially diluted 10-fold of each generation, for culturing at 37° C. for 2 days, to fix the individual cells and subsequently count the FFU by indirect FA and EIA. The cells were fixed by gently rinsing the cells sequentially in PBS and deionized water and immersing then the cells in acetone with addition of methanol at a final concentration of 10% (V/V) at ambient temperature for 5 minutes.

The FA was performed, by using anti-human rotavirus guinea pig hyperimmune serum for the primary reaction and FITC-labeled goat IgG (manufactured by Cappel, Co., USA) for the secondary reaction.

Meanwhile, EIA was practiced by individually using guinea pig hyperimune serum against the rotavirus of group A for the primary reaction and peroxidase-labeled anti-guinea pig IgG goat serum (manufactured by Cappel, Co., USA) for the secondary reaction; and the chromogenic reaction was carried out by using a substrate solution [4-chloro-1-naphthol (manufactured by Bio-Rad, Co., USA) at a final concentration of 1 mg/ml, 20% (V/V) methanol and Tris-HCl buffer containing 35% (V/V) aqueous hydrogen peroxide at a 1/1000 volume].

The results of the FFU counting as described above are shown in Table 2. The adaptation of the rotavirus to each cloned cell strain highly permissive, as recovered in Example 1, was promoted in a smooth fashion, and a passaged virus with an infected virus volume in log (in unit FFU/ml) of 6.5 or more was stored as a cloned Vero cell-adapted virus strain at −80° C.

TABLE 2

| Number of virus passage | Cloned cell strain | | | Comparative control |
|---|---|---|---|---|
| | Vero CL-9 | Vero CL-16 | Vero CL81-7 | Vero CCL81 |
| 1 | 5.3 | 4.8 | 5.1 | 2.7 |
| 2 | 5.8 | 5.3 | 5.5 | 2.7 |
| 3 | 6.0 | 5.4 | 5.7 | 2.8 |
| 4 | 6.7 | 6.0 | 6.2 | — |
| 5 | 6.9 | 6.1 | 6.4 | — |
| 6 | 7.2 | 6.2 | 6.6 | — |
| 7 | 7.3 | 6.5 | 6.8 | — |

Numerical figure: in log (FFU/ml).
—: not practiced.
Vero CCL 81: Vero cell (ATCC CCL 81) prior to cloning.

EXAMPLE 3

(1) Isolation of Novel Human Rotavirus Strain AU64n

AGMK (African Green Monkey Kidney) cells were cultured in a culture test tube in the same manner as in Example 1, to form a monosheet, and thereafter, the medium was exchanged to a fresh non-serum-added MEM the day preceding the inoculation of a virus isolation material described below.

On the other hand, a virus isolation material was prepared as follows. Diarrhea feces (0.1 g) from an infant infected with rotavirus was suspended in 0.9 ml of MEM, and into the resulting suspension was added and mixed the aforementioned trypsin type IX to a final concentration of 10 µg/ml, which was then kept warm at 37° C. for 20 minutes. Subsequently, the suspension was urged with a micro high-speed centrifuge at 10,000 rpm for 30 seconds, and the resulting supernatant was collected and diluted 10-fold with MEM, and then, the dilution was passed through a filter of a diameter of 0.22 µm for disinfection. The filtrate was diluted serially 10-fold in a virus proliferation medium (MEM supplemented with trypsin type IX at a final concentration of 0.5 µg/ml), and the resulting solution was defined as a virus isolation material.

After the medium for the AGMK cells was discarded, 1 ml each of the virus isolation material described above was added to the cells in each test tube. The tube was kept warm at 37° C. for one hour, to adsorb the virus in the isolation material onto the cells, and subsequently, the inoculation solution was discarded. The cells were rinsed once in the virus proliferation medium (1 ml/tube). After discarding the rinse solution, then, a fresh virus proliferation medium (1 ml/tube) was added to the individual cells, for roller tube culture. By freezing and thawing the cells with CPE observed during the culture, together with the culture fluid, a sample was prepared. By ELISA (Example 1), the rotavirus antigen was assayed in each sample, and then, a sample positive with the antigen was recovered. The supernatant of the sample centrifuged at a low speed was subjected as a primary virus to the following passage.

(2) Passage of Novel Human Rotavirus Strain

Trypsin type IX was added and mixed into the primary virus, for incubation at 37° C. for 90 minutes (referred to as "virus activation" hereinbelow), and the resulting solution was diluted 10-fold with MEM, and in the same manner described above in (1), the dilution was inoculated and cultured in fresh cells described below, for continuous passaging of the virus. Consequently, a human rotavirus strain comprising 5 passages in AGMK cells, subsequent 5 passages in Vero cells (ATCC CCL 81) and additional 2 passages in Vero CL-9 cells (FERM BP-6028) (passage history is represented according to a principle, for example "AGMK/5, Vero CCL81/5, Vero CL-9/2" below).

The serotype and genotype of the freshly isolated human rotavirus strain were analyzed according to the analysis method of serotype and virus genome RNA by means of electrophoresis pattern, as described in the report by the present inventors (Microbiology and Immunology, 38(4), p.317–320, 1994). It was elucidated that the serotype and genotype were G1P1B[4]. Because the serotype and genotype are the same as those of the AU64 strain, according to the classification shown in Table 1, the novel human rotavirus strain was designated as AU64n.

(3) Adaptation of the AU64n Strain Virus to "AGMK/5, CCL81/5 and Vero CL-9/2"

The adaptation was carried out by plaque cloning as follows. Vero CL-9 cells were cultured in a 6-well Falcon plate (manufactured by Becton Dickinson, Co., USA) in a $CO_2$ incubator, until a monolayer of cells was formed. Then, the medium was replaced with a non-serum-added MEM, for additional culturing overnight. Subsequently, the AU64n strain virus activated with trypsin as described above was diluted 10-fold with the virus proliferation medium, and the resulting solution was inoculated at 1 ml/well into the cells. After adsorbing the virus onto the cells while keeping warm the mixture at 37° C. for one hour, the inoculation solution was discarded. Then, an agar medium [199 medium (manufactured by FMOBIO PRODUCTS, Co.) supplemented with agarose ME at a final concentration of 0.7% (W/V) and 0.5 µg/ml trypsin type IX] was overlaid at 2 ml/well, and after the solidification of the agar, the plate was turned upside down, to continue the culture. On day 4 and 7 after virus inoculation, individually, the agar medium was repeatedly overlaid to continue the culture, and on day 11, additionally, agar medium supplemented with addition of Neutral Red (manufactured by Wako Pure Chemical Industries, Co.) at a final concentration of 0.003 (W/V) was overlaid, for continuing the culture to form a plaque by cell staining. On day 12, an independently separated plaque with a larger diameter was collected (cloned). The plaque was suspended in MEM, and by the same method as for the virus passage described in (2), the virus was once amplified in Vero CL-9 cells, for subsequent another plaque cloning. After repeating the procedures of cloning and virus amplification three times in total, additionally, passaging over two generations were done in Vero CL-9 cells, followed by fourth plaque cloning and amplification, and the resulting AU64n strain virus was further passaged over one generation in Vero CL-9 cells, to prepare an original seed of the human rotavirus AU64n strain (the passage history is "AGMK/5, Vero CCL81/5, Vero CL-9/12"). The infectious titer on each passage level was assayed in log (FFU/ml) in the same manner as described in Example 2. The titers were as follows in the passaging order.

2.5, 3.7, 4.6, 5.4, 5.8 (passaged over 5 generations in AGMK);

2.8, 3.5, 3.6, 4.0, 4.4 (passaged over 5 generations in Vero CCL81);

5.9, 6.4, 6.8, 7.0, 7.1, 7.1, 7.1, 7.2, 7.2, 7.2, 7.2, 7.2, (passaged over 12 generations in Vero CL-9).

EXAMPLE 4

(1) Mass Culture of AU64n Strain Virus

By using 10 roller bottles at once, the virus was cultured at a mass scale, and the procedure was repeated eight times in total. More specifically, the culture medium of the Vero CL-9 cells after roller bottle culture with Falcon roller bottles (manufactured by Becton Dickinson, Co., USA; product number of 3027) was exchanged to non-serum-added MEM, for additional culturing overnight, and then, the culture medium was discarded. Into the cells in each bottle was inoculated the AU64n strain original seed recovered in Example 3, at 20 ml/bottle. Herein, the original seed was preliminarily activated with trypsin type IX. Subsequently, the cells were incubated under roller bottle culture at 37° C. for one hour, to adsorb the virus onto the cells, and the inoculation solution was then discarded, followed by addition of a fresh virus proliferation culture medium at 80 ml/bottle, for roller bottle culture at 37° C. for 2 days. After the termination of culturing, the culture in each bottle was frozen and thawed to prepare a virus suspension, which was then pooled. Thereafter, the virus suspension was centrifuged (3,000 rpm, 10 minutes), to recover the supernatant (800 ml per one culture), which was defined as a crudely purified virus suspension. The virus infectious titer ($\times 10^6$ FFU/ml) of each of the individually crudely purified virus suspensions, recovered through culture eight times in total, was assayed in the same manner as described in Example 3, (3). Consequently, the resulting titers in log (FFU/ml) were 4.9, 5.5, 10.0, 7.0, 7.5, 8.0, 4.2 and 4.0.

(2) Purification of AU64n Strain Virus

By using the crudely purified virus suspensions, 4 lots were prepared in total, each lot of 1.2 liters. The virus of each lot was purified as follows. The crudely purified virus suspension of each lot was centrifuged (10,000 rpm for 10 minutes), and the resulting supernatant was collected, followed by further ultracentrifugation (19,000 rpm, 6 hours), and the precipitate was suspended in 15 mM PBS, pH 7.5, to a final volume of 40 ml, which was a 30-fold concentrated solution. The concentrated solution was centrifuged (10,000 rpm, 10 minutes), and the supernatant was collected, which was then overlaid on a 30 (W/V) % sucrose cushion, for ultracentrifugation (38,000 rpm, 3 hours). After ultracentrifugation, the resulting precipitated fraction was again suspended in 15 mM PBS, pH 7.5, to recover the virus of a purified AU64n strain. The virus infectious titers of the 4 lots in total in re-suspension (6 ml/lot) were counted; simultaneously, the protein was assayed by the phenol reagent method. Consequently, the virus infectious titer ($\times 10^8$ PFU/ml) and [protein level (mg/ml)] were as follows; 3.8 [1.36] for #1; 4.8 [1.10] for #2; 3.3 [0.94] for #3; and 1.3[1.57] for #4.

(3) Inactivation of AU64n Strain Virus

From the individual lots (#1 through #4) were collected the re-suspension solutions (purified AU64n strain virus), each of 3 ml, and the pooled re-suspensions in total of 12 ml were diluted and adjusted with 15 mM PBS, pH 7.5 to a protein content of 100 µg/ml.protein, followed by addition of formalin to a final concentration of 0.1 (V/V) %, and the resulting solution was left to stand at 4° C. for 2 weeks. Then, the solution was dialyzed against 15 mM PBS, pH 7.5 at 5° C. for 30 hours. So as to verify the appropriateness of the inactivated virus-containing solution after completion of the dialysis as an inactivated rotavaccine bulk solution, a variety of tests were carried out. According to the Regulation "Japanese B Encephalitis Vaccine" defined in the Biological Formulation Standard, more specifically, protein content tests, coloring tests, sterile tests, inactivation tests and tests of the absence of abnormal toxicity were done, provided that the inactivation tests were conducted by using Vero CL-9 cells. Consequently, it was verified that the inactivated virus-containing solution was suitable as a vaccine bulk solution.

(4) Preparation of Vaccine Against Rotavirus Infections

The vaccine bulk solution was diluted with 15 mM PBS, pH 7.5, to adjust the protein content to 50 µg/ml, to prepare an inactivated AU64n vaccine. Meanwhile, 0.5 ml was collected from each of the non-inactivated 4 lots, and the pooled re-suspensions (purified AU64n strain virus) were adjusted to 50 μg/ml in the same manner as described above, and the resulting solution was defined as raw AU64n-containing solution.

(5) Assaying of Immunogenicity of Inactivated AU64n Vaccine

The inactivated AU64n vaccine was inoculated twice at a dose of 10 μg.protein/dose into ddy mice of age 4–5 weeks (7 animals) at an interval of 2 weeks, and on week 2, blood was drawn. As comparative controls, a raw AU64n-containing solution and 15 mM PBS, pH 7.5 both were used; the former was inoculated into 19 mice and the latter, into 10 mice, prior to blood collection. The neutralization antibody titer of each serum recovered for the AU64n strain was assayed by the 60% plaque reduction method. The results are shown in Table 3, which verifies the excellent immunogenicity of the resulting vaccine.

TABLE 3

| Antigen for immunization | Neutralization antibody titer ± confidence limits |
|---|---|
| Inactivated AU64n vaccine | 2.20 ± 0.23 |
| Raw AU64n-containing solution | 2.30 ± 0.12 |
| 15 mM PBS, pH 7.5 | ≦1.60 |

Neutralization antibody titer: geometric mean of antibody titers in common log of individual mice
Confidence limits: significance level 5%

(6) Immunization Performance of Inactivated AU64n Vaccine

By the 60% focus reduction method, the neutralization potency of the sera from 7 mice immunized with the inactivated AU64n vaccine against rotaviruses with different serotypes or genotypes was assayed. The results are shown in Table 4. It was indicated that the vaccine prepared by using the AU64n strain as the effective component showed efficiency for prevention against the infection not only with the AU64n strain but also with a strain Wa, with difference in both Serotype P and genotype from those of the strain, and a DS-1 strain with a different serotype G.

TABLE 4

| Challenge virus | Serotypes P and G [genotypes] | Neutralization antibody ± confidence limits |
|---|---|---|
| AU64n | G1P1B[4] | 2.19 ± 0.52 |
| Wa | G1P1A[8] | 2.43 ± 0.43 |
| DS-1 | G2P1B[4] | 1.90 ± 0.25 |

Neutralization antibody titer: geometric mean of antibody titers in common log of individual mice
Confidence limits: significance level 5%

EXAMPLE 5

Recovery of Novel Human Rotavirus Strain AU32n:

By the same method as described in Example 3, a novel human rotavirus strain was isolated and passaged to assay the infectious titer and analyze the serotype and genotype. More specifically, by using AGMK cells, human rotavirus strains were separated from diarrhea feces from a rotavirus-infected infant, and after the passage in the same cells over two generations, the strains were passaged in Vero CL-9 cells over 8 generations in total [first to third generations (plaque cloning), fourth generation (stationary culture), fifth generation (plaque cloning), sixth generation (stationary culture), seventh to eighth generations (roller bottle culture)], to recover a cloned cell-adapted human rotavirus strain (passage history is AGMK/3, Vero CL-9/8). The infectivity titer of the human rotavirus strain was 6.0 in log (FFU/ml). And, its serotype [genotype] was G9P1A [8], which was the same as those of the AU32 strain. Thus, the novel human rotavirus strain was designated as AU32n.

EXAMPLE 6

Isolation of Rotavirus in Vero CL-9:

By the same method as described in Example 3(1), rotavirus is to be isolated. However, the isolation procedure is carried out by using Vero CL-9 cells in place of AGMK cells.

The present invention provides a vaccine, a diagnostic agent, and a reagent, all relating to rotavirus infections, and methods for producing them, whereby the present invention can make contributions to human health, worldwide medical administrative management, environmental hygiene, cattle raising, and research works for the fundamentals and clinical practice and application of rotavirus infections. The present invention provides a vaccine as a strong prophylactic means against diseases drawing serious concern under the names of infant vomiting and diarrhea, white feces diarrhea, infant pseudo-cholera and the like. Hence, the present invention can give welfare expected for a long term, not only to individual homes worldwide but also to individual workers engaged in medicine and health care all around the world.

What is claimed is:

1. A method for producing a rotavirus antigen, which comprises:

cloning a cell strain from a cell culture, said cloned cell strain having at least a five-fold improvement in rotavirus proliferation than the uncloned cell culture;

passaging a rotavirus in the cloned cell strain and adapting the rotavirus to the cloned cell strain to prepare a cloned cell adapted-rotavirus strain;

culturing as a seed virus the adapted rotavirus strain or a reassortant prepared by using the adapted rotavirus strain as a parent strain; and isolating and purifying the rotavirus antigen from the culture medium of the seed virus.

2. The method according to claim 1, wherein the cell culture is a culture of Vero cells (ATCC CCL 81).

* * * * *